(12) United States Patent
Eischeid

(10) Patent No.: US 11,804,297 B1
(45) Date of Patent: Oct. 31, 2023

(54) COMPUTING SYSTEM FOR UPDATING OR ENTERING MULTIDIMENSIONAL VALUES

(71) Applicant: Allscripts Software, LLC, Raleigh, NC (US)

(72) Inventor: Todd Eischeid, Cary, NC (US)

(73) Assignee: Allscripts Software, LLC, Raleigh, NC (US)

( * ) Notice: Subject to any disclaimer, the term of this patent is extended or adjusted under 35 U.S.C. 154(b) by 1,000 days.

(21) Appl. No.: 15/457,212

(22) Filed: Mar. 13, 2017

(51) Int. Cl.
G16H 40/63 (2018.01)
G16H 10/60 (2018.01)

(52) U.S. Cl.
CPC .............. G16H 40/63 (2018.01); G16H 10/60 (2018.01)

(58) Field of Classification Search
CPC ............... G16H 40/63; G16H 10/60
See application file for complete search history.

(56) References Cited

U.S. PATENT DOCUMENTS

| | | | |
|---|---|---|---|
| 7,772,479 B2 | 8/2010 | Kobayashi | |
| 8,645,864 B1 | 2/2014 | Wright | |
| 8,812,992 B2* | 8/2014 | Im | G06F 3/1438 715/764 |
| 2006/0095147 A1 | 5/2006 | Van De Kerkhof et al. | |
| 2012/0054686 A1 | 3/2012 | Joo et al. | |
| 2013/0031497 A1* | 1/2013 | Arrasvuori | G06F 3/0488 715/764 |
| 2013/0097551 A1* | 4/2013 | Hogan | G06F 3/0488 715/780 |
| 2014/0313135 A1* | 10/2014 | Pisters et al. | G06F 3/04883 345/173 |
| 2015/0202533 A1* | 7/2015 | Eng et al. | A63F 13/42 463/31 |
| 2015/0248212 A1* | 9/2015 | Breedvelt-Schouten et al. | G06Q 10/10 715/850 |
| 2016/0019360 A1* | 1/2016 | Pahwa et al. | G16H 80/00 705/3 |

* cited by examiner

*Primary Examiner* — Fonya M Long
*Assistant Examiner* — Anthony Balaj
(74) *Attorney, Agent, or Firm* — CALFEE, HALTER & GRISWOLD LLP

(57) ABSTRACT

Described herein are features pertaining to updating patient data based upon input of an EHR user by way of a GUI. The GUI can depict health information that is generated or extracted from the patient data, wherein the health information can include demographic information, vital statistics, etc. of a patient. The GUI receives input with respect to a multidimensional value displayed on the GUI, the input comprising input in a first dimension and input in a second dimension, the multidimensional value comprising a first value and a second value. The first value and the second value are simultaneously modified based upon the input in the first dimension and the input in the second dimension.

20 Claims, 9 Drawing Sheets

COMPUTING SYSTEM FOR UPDATING OR ENTERING MULTIDIMENSIONAL VALUES

BACKGROUND

Electronic health record applications (EHRs) are robust applications that are utilized in medical facilities across a variety of aspects of a medical practice. For example, and not by way of limitation, an EHR can include functionality related to patient intake, billing, updating medical records, prescribing medication, tracking care over time, and so forth. Computer-executable applications have been developed that allow an EHR user to review health information related to a patient by way of, for example, a graphical user interface (GUI) on a display. Further, the applications often allow the EHR user to update or enter values in the health information.

Generally, the health information comprises values that are indicative of various categories related to the patient's health (e.g., weight, blood pressure, etc.). A value in the values can be a multidimensional value (e.g., a value that has sub-values, a value that includes multiple measurements, etc.). An example of a multidimensional value is blood pressure, which comprises a systolic blood pressure dimension and a diastolic blood pressure dimension. Conventionally, the applications facilitate updating or entering each dimension (of a multidimensional value) in sequential order. In the blood pressure example, to update a blood pressure value for a patient, the EHR user would have to update or enter (by, e.g., touch input) the systolic blood pressure dimension, followed by the diastolic pressure dimension.

SUMMARY

The following is a brief summary of subject matter that is described in greater detail herein. This summary is not intended to be limiting as to the scope of the claims.

Described herein are various technologies pertaining computer executable applications that are well-suited for use in a healthcare environment. More particularly, described herein are various technologies pertaining to a computer system, wherein a computer-executable client EHR is configured to cause health information to be displayed to an EHR user, wherein the health information can include demographic information, vital statistics, etc. of a patient, and further wherein the EHR user can review, enter, or update parts (e.g., values) of the health information. The health information can be stored as patient data at a server computing device that executes a server EHR. Subsequent to displaying the health information to the EHR user, the client EHR is configured to receive input from the EHR user (e.g., a touch gesture), wherein the input includes an indication that the EHR user is entering or updating a part of the health information. The client EHR is configured to locally display changes to the health information (based upon the input of the EHR user) as well as transmit a request to the server EHR, wherein the request causes the patient data (from which the health information is generated or extracted) to be modified or entered.

Additionally, a part of the health information can be a multidimensional value, where a multidimensional value is a value that includes multiple dimensions (e.g., a value that has sub-values, a value that includes multiple measurements, etc.). For example, a blood pressure for the patient has two dimensions: a systolic blood pressure and a diastolic blood pressure. The client EHR is configured to allow the EHR user to simultaneously enter or update the multiple dimensions (of a multidimensional value) in the health information (as well as cause the patient data, from which the multidimensional value is generated or extracted, to be modified). More particularly, the client EHR is configured to 1) identify when the EHR user inputs an indication that the EHR user is updating or entering the multidimensional value; 2) determine which dimensions of the multidimensional value are being updated or entered; 3) update or enter the dimensions based upon the input; and 4) cause the patient data (from which the multidimensional value is generated or extracted) to be modified.

The client EHR can be configured to cause an assistant overlay pane to be displayed when the EHR user inputs an indication that the EHR user is entering or updating the multidimensional value. The assistant overlay pane can include information related to helping the EHR user understand dimensions of the multidimensional value (to, e.g., aid the EHR user in choosing a desired value). Further, the client EHR can be configured to cause a selection pane to be displayed when the EHR user indicates that the user is updating or entering a number of dimensions of the multidimensional value that is less than a number of total dimensions that the multidimensional value includes. More particularly, the selection pane allows the EHR user to select which dimensions of the multidimensional value to update or enter.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
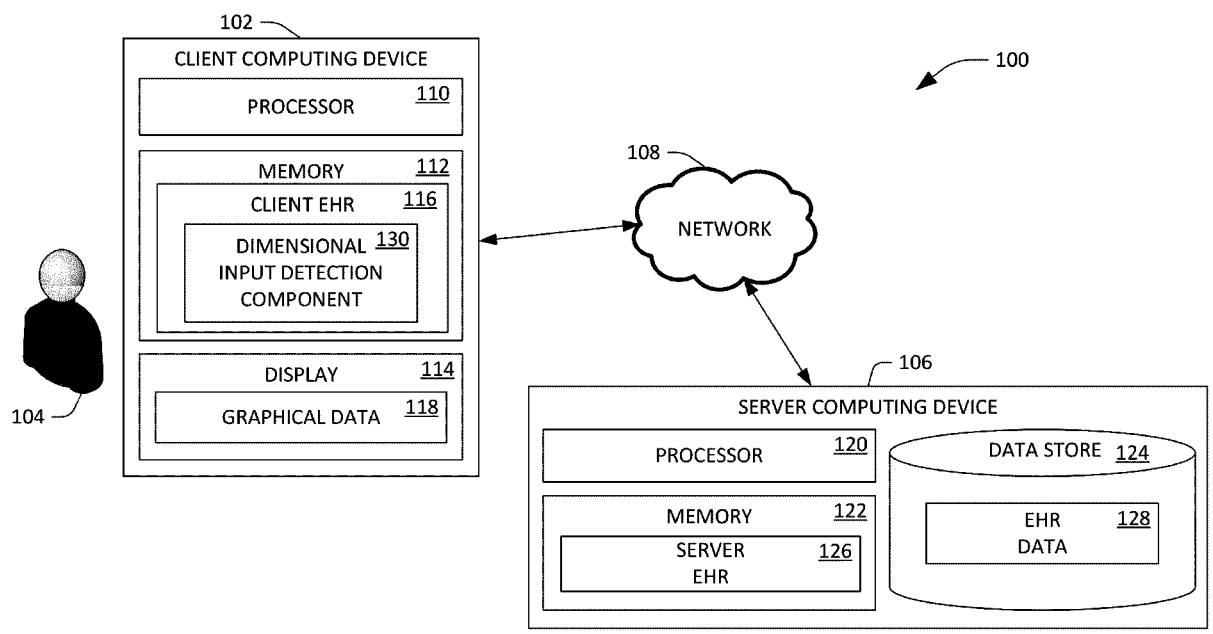
FIG. 1 is a functional block diagram of an exemplary system that facilitates updating patient data based upon input of an EHR user by way of a graphical user interface.

Various technologies pertaining to a system that displays a graphical user interface that depicts health information that is generated based upon patient data, facilitates modifications to values in the health information, and modifies the patient data based upon the modifications are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Further, as used herein, the term "exemplary" is intended to mean serving as an illustration or example of something, and is not intended to indicate a preference.

Further, as used herein, the terms "component" and "system" are intended to encompass instructions stored in computer-readable data storage that are configured to cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Generally, an EHR is a distributed application that includes a client EHR executing on a client computing device and a server EHR executing on a server computing device. The client EHR, briefly, is configured to display data to an EHR user and receive input from the EHR user, while the server EHR is configured to acquire or store data based upon information received by the client EHR from the EHR user and transmit information to the client EHR for presentment to the EHR user by way of the client EHR.

Summarily, the features described herein pertain to technologies for a client EHR that is configured to display health information to an EHR user, wherein the health information can include demographic information, vital statistics, etc. of a patient, and further wherein the EHR user can review, enter, or update parts of the health information. The health information can be stored as patient data on the server EHR. Subsequent to displaying the health information to the EHR user, the client EHR is configured to receive input from the EHR user, wherein the input includes an indication that the EHR user is entering or updating a part of the health information. The client EHR is configured to locally display changes to the health information (based upon the input of the EHR user) as well as transmit a request to the server EHR, wherein the request causes the patient data (from which the health information is generated or extracted) to be modified.

With reference now to FIG. 1, an exemplary system 100 that facilitates updating patient data based upon input of an EHR user by way of a GUI is illustrated. The system 100 includes a client computing device 102 that is operated by an EHR user 104 (e.g., a clinician, billing specialist, etc.). The client computing devices 102 operated by the EHR user 104 may be any suitable type of client computing device, including a desktop computing device, a laptop computing device, a mobile telephone, a tablet computing device, a wearable computing device, or the like. Generally, the EHR user 104 may be utilizing the client computing device 102 to, for example, provide care to a patient, perform patient intake, update billing or medical records, prescribe medication, track care over time, etc. In an example, the EHR user 104 may be a healthcare provider that is utilizing the client computing device 102 in connection with providing care to a patient, where the healthcare provider can review, enter, or update health information (e.g., heartrate, blood pressure, etc.) of the patient. As will be described in greater detail herein, a part of the health information can be a multidimensional value, where a multidimensional value is a value that includes multiple dimensions (e.g., a value that has sub-values, a value that includes multiple measurements, etc.). For example, blood pressure for the patient has two dimensions: a systolic blood pressure and a diastolic blood pressure.

The system 100 further includes a server computing device 106 that is in communication with the client computing device 102 by way of a suitable network 108, such as the Internet, an intranet, or the like. While the client computing device 102 is depicted as being in communication with the server computing device 106 by way of the network 108, it is to be understood that the client computing device 102 may be in communication with the server computing device 106 over different networks. Further, the server computing device 106 can be an enterprise device whose operation is controlled by a healthcare enterprise. In another example, the server computing device 106 can be a cloud-based computing device, where maintenance and operation of the server computing device 106 is handled by a company that provides the EHR for use by a healthcare enterprise.

The client computing device 102 includes a processor 110, memory 112, and a touch-sensitive display 114. The memory 112 stores instructions that are executed by the processor 110. More specifically, the memory 112 includes a client EHR 116. The client EHR 116 is configured to, as the EHR user 104 utilizes the client computing device 102, cause graphical data 118 to be displayed on the display 114, wherein the graphical data 118 can include data that is relevant to activities performed by the EHR user 104 (e.g., entering health information of a patient). Additionally, as will be described in greater detail herein, the client EHR 116 includes a dimensional input detection component 130. The dimensional input detection component 130 can be configured to receive input from the EHR user 104 (e.g., by way of a GUI that is displayed in the graphical data 118). Based upon the input, the dimensional input detection component 130 can transmit data to or receive data from the server computing device 106. Transmitted data can include requests for patient data (e.g., that comprises the health information of the patient) or instructions to update or enter the patient data. While the display 114 is depicted as being integral to the client computing device 102, it is to be understood that the display 114 may be externally coupled to the client computing device 102 or may be a projected display.

The server computing device 106 includes a processor 120, memory 122 that stores instructions that are executed by the processor 120, and a data store 124. As shown in FIG. 1, the memory 122 includes a server EHR 126. The server EHR 126 is configured to transmit data to and receive data from the client computing device 102. More particularly, the server EHR 126 is configured to respond to requests for the patient data (from which the health information can be generated or extracted) and to execute instructions (received from the client computing device 102) to update or enter the patient data. The patient data can be stored as part of EHR data 128 that is retained in the data store 124.

Operation of the client EHR 116 and the server EHR 126 is now described. As noted previously, the client EHR 116 is configured to receive input from the EHR user 104 at the client computing device 102. The input can include an indication that the EHR user 104 is reviewing, entering, or updating health information (that can be generated or extracted from the EHR data 128 that is stored on the server computing device 106). Responsive to the EHR user 104 indicating that the EHR user 104 is reviewing, entering, or updating the health information of the patient, the client EHR 116 is configured to transmit a request to the server computing device 106, where the request includes a request for data about the patient included in the EHR data 128. Responsive to receiving the request, the server EHR 126 is configured to retrieve (e.g., from the data store 124) and transmit the requested patient data to the client computing device 102. Responsive to receiving the requested patient data, the client EHR 116 is configured to generate (or extract) health information from the patient data and to display the health information in the graphical data 118 (on the display 114) to the EHR user 104.

As will be described in greater detail below, the client EHR 116 can be configured to, subsequent to displaying the health information of the patient in the graphical data 118, receive additional input from the EHR user 104. The additional input can comprise an indication that the EHR user 104 is modifying a value in the health information. Responsive to receiving the additional input, the client EHR 116 can be configured to locally display the modification of the EHR user 104 (e.g., on the client computing device 102) as well as transmit a request to the server computing device 106, wherein the request causes the modification of the EHR user 104 (in the health information) to occur in the patient data (from which the health information is generated or extracted).

Figure 2:
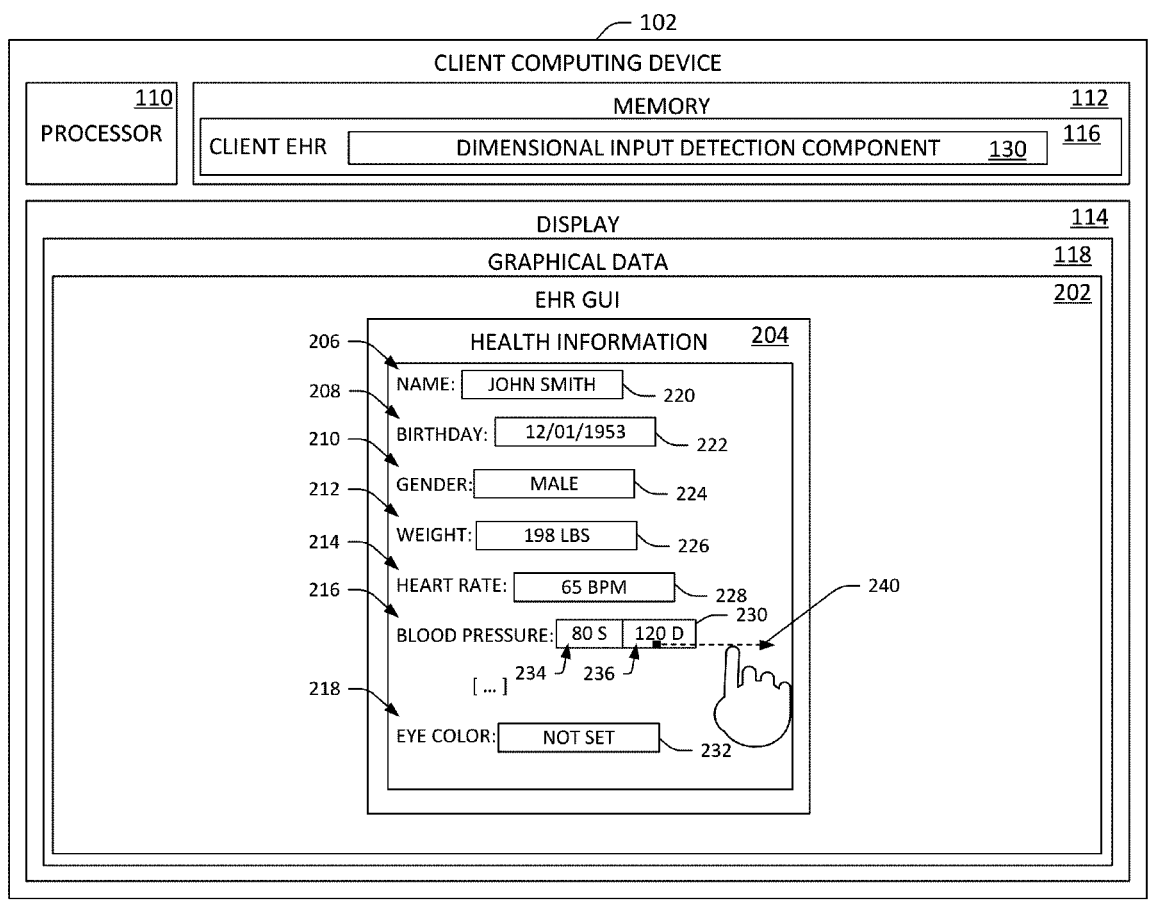
FIG. 2 depicts an exemplary client computing device.

With reference now to FIG. 2, a functional block diagram of the client computing device 102 is illustrated. As indicated previously, the client EHR 116 is loaded in the memory and executed by the processor 110. The processor 110, when executing the client EHR 116, causes an EHR GUI 202 to be included in the graphical data 118 on the display 114. In this example, the EHR GUI 202 includes a health information pane 204 that can be presented when the client EHR 116 receives an indication that the EHR user 104 is reviewing, entering, or updating a patient's health information that is stored as the patient data (e.g., as part of the EHR data 128 on the server computing device 106). The health information pane 204 includes fields and respective value indicators that can be indicative of, for example, information of the patient. More particularly, the fields indicate a category of information (e.g., demographic, medical, etc.) that the EHR can record about a patient, and the respective value indicators indicate and include details of the patient (for a particularly category of information).

In the example shown in FIG. 2, the health information pane 204 includes a "NAME" field 206, a "BIRTHDAY" field 208, a "GENDER" field 210, a "WEIGHT" field 212, a "HEART RATE" field 214, a "BLOOD PRESSURE" field 216, and an "EYE COLOR" field 218. For each field in the fields 206-218, the health information pane includes value indicators 220-232, wherein a value indicator in the value indicators 220-232 indicates a value (e.g., measurement, entry, etc.) for a respective field. For example, a first value indicator 224 can include a value of "MALE" (for the "GENDER" field 210) for a patient that the EHR user 104 is treating while utilizing the client computing device 102. The first value indicator 224 indicates that the patient is male. Further, a value indicated by a value indicator can be a multidimensional value, wherein the multidimensional value is a value that includes multiple dimensions (e.g., a value that has sub-values, a value that includes multiple measurements, etc.). For each dimension (of the multidimensional value), the client EHR health information pane 204 can include a dimensional indicator that indicates a value for the dimension. For example, for the "BLOOD PRESSURE" field 216, a second value indicator 230 includes two dimensional indicators: 1) a first dimensional indicator 234 that indicates a systolic blood pressure of a patient, and 2) a second dimensional indicator 236 that indicates a diastolic blood pressure of the patient.

Additionally, when a value indicator in the value indicators 220-232 is selected by the EHR user 104 (e.g., by way of a mouse pointer, voice command, interaction with a touch sensitive display, etc.), the client EHR 116 is configured to, by way of the EHR GUI 202, facilitate updating or entering of a value in the value indicator. The client EHR 116 can facilitate updating or entering of the value (in a value indicator) by, for example, receiving, from the EHR user 104 an input of the value on a keyboard or a selection of the value in a drop-down list.

In lieu of facilitating the updating or entering a multidimensional value in a value indicator by conventional methods, the client EHR 116 can be configured to update or enter the multidimensional value (in a value indicator) based upon multi-dimensional input from the EHR user 104. More particularly, the dimensional input detection component 130 is configured to detect whether the EHR user 104 has caused an indication that the EHR user 104 is updating or entering a multidimensional value for a value indicator in the value indicators 220-232 that includes the multidimensional value. In an exemplary embodiment, the dimensional input detection component 130 can be configured detect whether the EHR user 104 is updating or entering the multidimensional value based upon tags that are assigned to the value indicators 220-232 a priori, where the tags allow the dimensional input detection component 130 to identify whether a value indicator in the value indicators 220-232 includes a multidimensional value. In the example shown in FIG. 2, the dimensional input detection component 130 detects that the EHR user 104 is updating a multidimensional value in the second value indicator 230 responsive to 1) the EHR user 104 tapping on and holding the second value indicator 230 for a predetermined number of time (e.g., one second); and 2) the dimensional input detection component 130 identifying that the second value indicator 230 has been assigned a tag (not shown), where the tag indicates that the second value indicator 230 includes a multidimensional value. In the example, the EHR user 104 tapping on the first value indicator 224 refrains from causing the dimensional input detection component 130 to detect that the EHR user 104 is updating or entering a multidimensional value because the first value indicator 224 does not have the tag assigned to it.

Responsive to detecting that the EHR user 104 has caused an indication that the EHR user 104 is updating or entering the multidimensional value, the dimensional input detection component 130 is configured to determine a number of dimensions (of the multidimensional value) that the user is updating or entering based upon the input from the user. More specifically, the dimensional input detection component 130 can be configured to detect that the EHR user 104 is updating or entering a single dimension of the multi-dimensional value (e.g., either the first dimensional indicator 234, indicative of the systolic blood pressure of a patient, or the second dimensional indicator 236, indicative of the diastolic blood pressure of the patient) when, as shown in FIG. 2, the EHR user 104 taps and holds on the second value indicator 230 with a single finger (e.g., an index finger). In other embodiments, the dimensional input detection component 130 can detect that the EHR user 104 is updating or entering the single dimension when the EHR user 104 clicks and holds a single mouse button on the second value indicator 230, when the EHR user 104 stares at the second value indicator 230 for a predetermined amount of time (measured by, e.g., eye tracking technology), etc.

Figure 3:
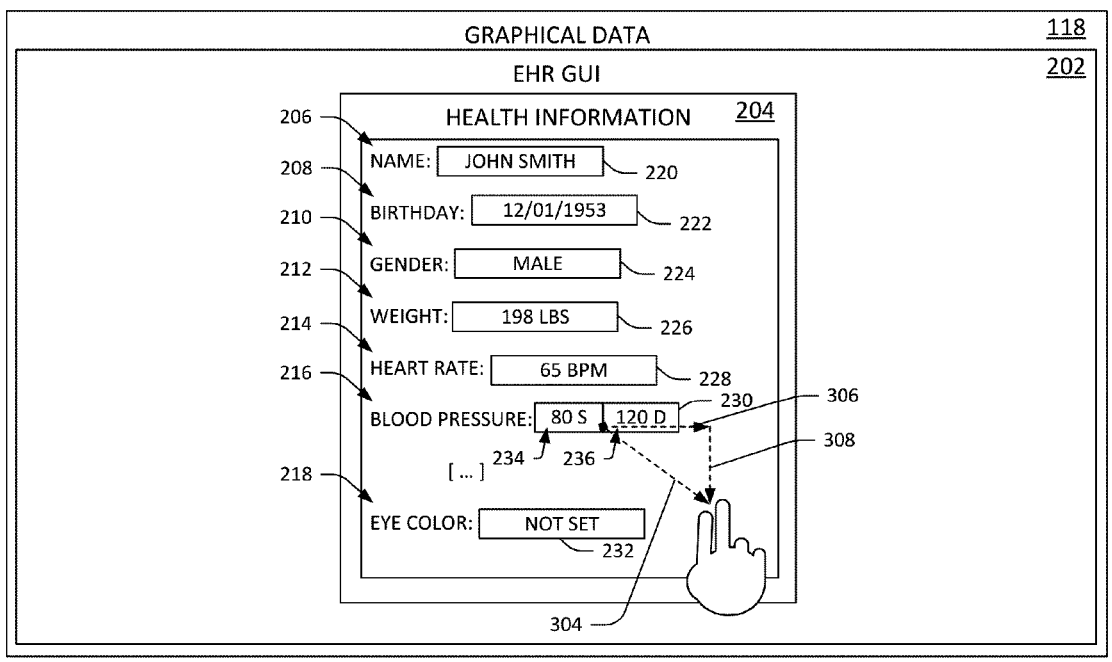
FIG. 3 is an exemplary graphical user interface of an EHR.

Turning to FIG. 3, the dimensional input detection component 130 can additionally be configured to detect that the EHR user 104 intends to simultaneously update or enter two dimensions of the multidimensional value at the same time (e.g., values in both the first dimensional indicator 234 and the second dimensional indicator 236 of the second value indicator 230). For example, the dimensional input detection component 130 can be configured to detect that the EHR user 104 is simultaneously updating or entering the two dimensions when the EHR user 104 taps and holds on the second value indicator 230 with two fingers (e.g., an index finger and a middle finger). In other embodiments, the dimensional input detection component 130 can detect that the EHR user 104 is simultaneously updating or entering the two dimensions when the EHR user 104 clicks and holds two buttons on a mouse button (e.g., a primary button and a secondary button) on the second value indicator 230, when the EHR user 104 clicks and holds a single mouse button while holding a key on a keyboard (e.g., a control key), etc.

Further, and as will be described in greater detail herein, it is contemplated that the dimensional input detection component 130 can be configured to detect that the EHR user 104 is simultaneously updating or entering three or more dimensions of a multidimensional value that includes three or more dimensions. For example, the dimensional input detection component 130 can be configured to detect that the EHR user 104 is updating or entering three dimensions when the EHR user 104 taps and holds on the value indicator (that includes a multidimensional value) with three fingers (e.g., an index finger, a middle finger, and a ring finger). In other embodiments, the dimensional input detection component 130 can detect that the EHR user 104 is updating or entering the three dimensions when the EHR user 104 clicks and holds two buttons on a mouse button (e.g., a primary button and a secondary button) on the value indicator (that includes a multidimensional value) while holding a key on a keyboard (e.g., a control key), when the EHR user 104 clicks and holds a single mouse button on the value indicator (that includes a multidimensional value) while holding two keys on a keyboard (e.g., a control key and a shift key), etc.

Returning to FIG. 2, in addition to determining the number of dimensions (of the multidimensional value) that the EHR user 104 is updating or entering, the dimensional input detection component 130 is configured to identify which dimension(s) (of the multidimensional value) is being updated or entered by the EHR user 104. In the example shown in FIG. 2, responsive to determining that the EHR user 104 (by using the single finger) has indicated that the EHR user 104 is updating or entering the single dimension, the dimensional input detection componetn 130 can identify which dimension(s) of the multidimensional value (e.g., either the first dimensional indicator 234 or the second dimensional indicator 236) based upon a location of the single finger 238 of the EHR user 104 relative to the GUI shown in FIG. 2. In the example, a touch and drag 240 of the EHR user 104 across a surface of the display begins in a region of the second value indicator 230 that includes the second dimensional indicator 236 (that is indicative of the diastolic blood pressure of the patient). Because the touch and drag 240 begins at the second dimensional indicator 236, the dimensional input detection component 130 identifies that the EHR user 104 is updating or entering a value for patient data (e.g., stored as part of the EHR data 128 on the server computing device 106) that is indicative of a diastolic blood pressure of the patient.

Responsive to identifying that the EHR user 104 is updating or entering the (single) value indicated by the second dimensional indicator 236 (the diastolic blood pressure of the patient), the dimensional input detection component 130 is configured to measure and/or calculate the value based upon the input of the EHR user 104. In the example shown in FIG. 2, the dimensional input detection component 130 can be configured to monitor a change in an (horizontal) x-axis for the touch and drag 240 of the EHR user 104 (e.g., a measurement of the difference in a starting pixel position for an initial touch and a current pixel position of a finger that is in contact with the display). Based upon the change in position of the finger along the x-axis, the dimensional input detection component 130 can cause the value in the second dimensional indicator 236 to increase or decrease. For example, as shown in FIG. 2, the dimensional input detection component 130 can be configured to increase the value as the touch and drag 240 goes to the right. Further, the value can decrease as the touch and drag 240 goes to the left. It is to be understood the dimensional input detection component 130 can be configured to cause the value in the second dimensional indicator 236 to increase or decrease based upon alternatives to the change in position of the finger along the x-axis of the touch and drag 240, e.g., a measurement of pressure of the touch input of the EHR user 104, a measurement of acceleration of the touch and drag 240, etc. Further, responsive to the EHR user 104 ceasing the input (e.g., the touch and drag 240), the dimensional input detection component 130 is configured to cause the patient data that is indicative of a diastolic blood pressure of the patient to be updated or entered by, e.g., a request that is transmitted to the server computing device 106.

Further, with reference again to FIG. 3, responsive to determining that the EHR user 104 (by using the two finger 302) has indicated that the EHR user 104 is updating or entering the two dimensions of the multidimensional value at the same time, the dimensional input detection componetn 130 can identify which dimensions of the multidimensional value (e.g., the first dimensional indicator 234 and the second dimensional indicator 236) are being updated or entered by the EHR user 104. In the example show in FIG. 3, the second value indicator 230 includes only two dimensional indicators (the first dimensional indicator 234 and the second dimensional indicator 236). Consequently, the dimensional input detection component 130 identifies that the EHR user 104 is updating or entering values for data (e.g., stored on the server computing device 106) that is indicative of a systolic blood pressure and the diastolic blood pressure of the patient. As will be described in greater detail below, in embodiments where the second value indicator 230 includes a multidimensional value that comprises more than two dimensional indicators (when the EHR user 104 has indicated that it is updating or entering two dimensions), the dimensional input detection component 130 can be configured to generate a selection pane, where the selection pane allows the EHR user 104 to identify (by, e.g., touch input) which dimensional indicators it is updating or entering.

Responsive to identifying that the EHR user 104 is updating or entering the two dimensions of a multidimensional value (e.g., the systolic blood pressure and diastolic blood pressure of the patient), the dimensional input detection component 130 is configured to measure and/or calculate values for the two dimensions based upon the input of the EHR user 104. In the example shown in FIG. 3, a second touch and drag 304 of the EHR user 104 begins in a region of the second value indicator 230. The dimensional input detection component 130 assigns a first finger (e.g., an index finger of the two fingers touching the display) to the first dimensional indicator 234 and a second finger (e.g., a middle finger of the two fingers) to the second dimensional indicator 236. Further, the dimensional input detection component 130 is configured to, respectively, monitor a first change in an (horizontal) x-axis 306 and a second change in a (vertical) y-axis 308 for the second touch and drag 304 of the EHR user 104. Based upon the change in the x-axis 306 and the change in the y-axis 308, the dimensional input detection component 130 can, respectively, cause values in the first dimensional indicator 234 and the second dimensional indicator 236 to increase or decrease. For example, when the EHR user 104 is utilizing the client computing device 102 to update a blood pressure measurement for the patient, as shown in FIG. 3, the dimensional input detection component 130 can be configured to simultaneously increase a first value in the dimensional indicator 234 and decrease a second value in the second dimensional indicator 236 as the second touch and drag 304 (by the EHR user 104) is directed down and to the right. In the example, if the EHR user 104 directed the second touch and drag 304 upwards and to the right, then the dimensional input detection component 130 can be configured to simultaneously increase a first value in the first dimensional indicator 234 and increase a second value in the second dimensional indicator 236. Because, in this example, two fingers are used when performing the touch and drag, the dimensional input detection component 130 can utilize a variety of approaches when detecting the change in positions along the x and y axes. For instance, the dimensional input detection component 130 can define a center point between the touchpoints of the first and second finger, and can track the movement of the center point as the first and/or second touchpoints change position in the x and/or y axes. In another example, the dimensional input detection component 130 can track either the touchpoint for the first finger or the touchpoint for the second finger, and track such touchpoint over time when simultaneously entering or updating multiple dimensions of a multidimensional value (i.e., both values are altered based upon movement of one of the touchpoints). In still yet another example, the dimensional input detection component 130 can track the touchpoints separately, and can update a first value based upon a change along the x axis of the first touchpoint, and can update a second value based upon a change along the y axis of the second touchpoint.

It is to be understood that the dimensional input detection component 130 can be configured to cause the values in either the first dimensional indicator 234 or the second dimensional indicator 236 to increase or decrease based upon alternatives to the change in the x-axis 306 or the change in the y-axis 308, e.g., a measurement of pressure of the touch input of the EHR user 104, a measurement of acceleration of the second touch and drag 304, etc. Further, responsive to the EHR user 104 ceasing the input (e.g., the second touch and drag 304), the dimensional input detection component 130 is configured to cause the patient data that is indicative of systolic blood pressure and a diastolic blood pressure of the patient to be updated or enter by, e.g., a request that is transmitted to the server computing device 106.

Figure 4:
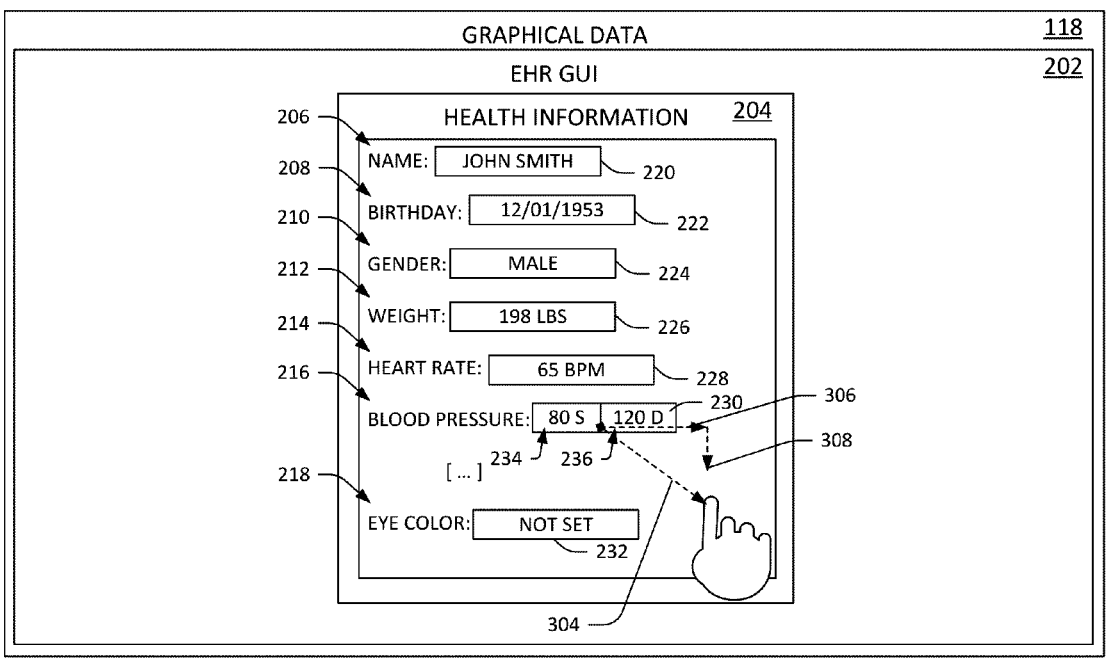
FIG. 4 depicts another exemplary graphical user interface of an EHR.

Additionally, it is contemplated that the EHR user 104 may remove one of the two fingers 302 during the second touch and drag 304. Turning to FIG. 4, subsequent to assigning the first finger to the first dimensional indicator 234 and the second finger to the second dimensional indicator 236, the dimensional input detection component 130 monitors the first change in position of the fingers along the x-axis 306 and the second change in position of the fingers along the y-axis 308 for the second touch and drag 304 of the EHR user 104. During the second touch and drag 304, the EHR user 104 can cease touch of its second finger, while maintaining touch with its first finger. The dimensional input detection component 130 can, accordingly, be configured to increase the first value in the dimensional indicator 234 as the second touch and drag 304 (by the EHR user 104) is directed down and to the right but only decrease the second value in the second dimensional indicator 236 while the touch of the second finger is maintained. Additionally, it is contemplated that the EHR user 104 can, after ceasing the touch of the second finger, re-engage the touch of the second finger. Responsive to detecting that the EHR user 104 has re-engaged the touch of the second finger, the dimensional input detection component can be configured to continue modifying the second dimensional indicator 236 based upon movement of the second finger across the display.

Figure 5:
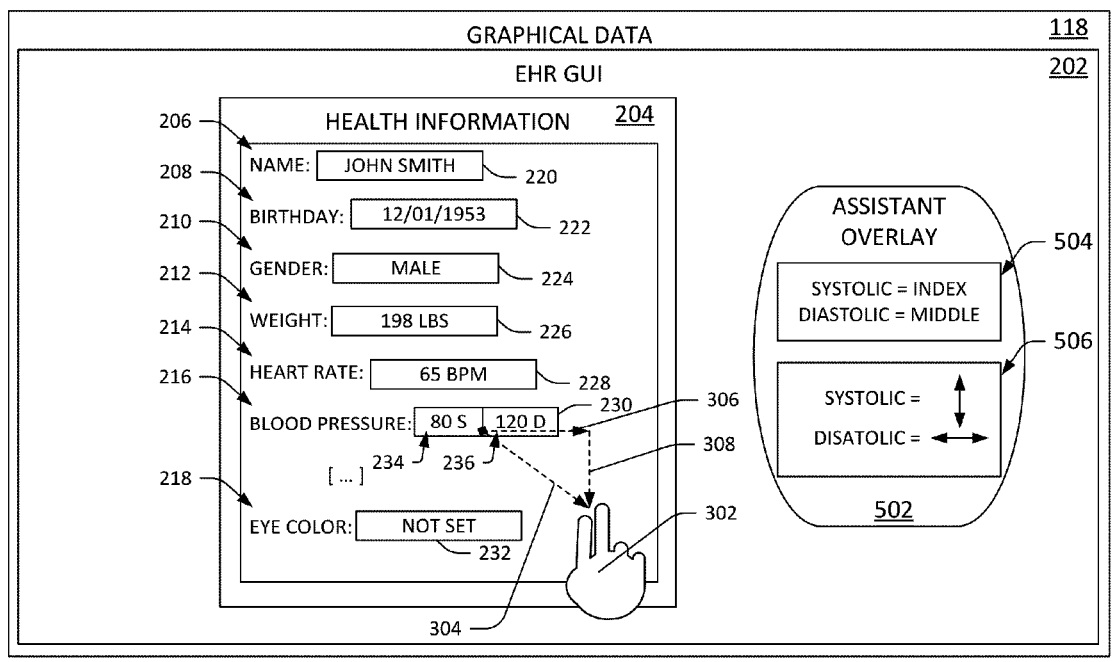
FIG. 5 depicts an exemplary assistant overlay pane.

Turning to FIG. 5, the client EHR 116 can be configured to cause an assistant overlay pane 502 to be displayed while the dimensional input detection component 130 is being executed by the processor 110. More particularly, the assistant overlay pane 502 can be displayed when the dimensional input detection component 130 detects that the EHR user 104 is updating or entering a multidimensional value in a value indicator (of the value indicators 220-232). The assistant overlay pane 502 can, as shown in FIG. 5, be displayed alongside the health information pane 204. The assistant overlay pane 502 can include information related to helping the EHR user 104 understand dimensions of a multidimensional value (to, e.g., aid the EHR user 104 in choosing a desired value). In other words, the assistant overlay pane 502 can include assignment information indicative of how the dimensional input detection component 130 has assigned a first finger (e.g., an index finger of the two fingers 302) to the first dimensional indicator 234 and a second finger (e.g., a middle finger of the two fingers 302) to the second dimensional indicator 236. In the example, the assignment information is indicated by text 504, where the text includes "SYSTOLIC = INDEX" and "DIASTOLIC = MIDDLE".

Additionally, the assistant overlay pane 502 can include coordinate information that is indicative of how the EHR user 104 can alter values in dimensions based upon changes in positions of fingers along the x-axis 306 and the y-axis 308. In the example shown in FIG. 5, the coordinate information is indicated by a graphic 506, wherein the graphic 506 indicates that the change in finger position along the x-axis 306 alters the value of the first dimensional indicator 234 (a systolic blood pressure) and that the change in finger position along the y-axis 308 alters the value in the second dimensional indicator 236 (a diastolic blood pressure).

In another embodiment, the assistant overlay pane 502 can be imposed on a region where the EHR user 104 causes an input to enter or update the multidimensional value. In other words, the assistant overlay pane 502 can be displayed where the input (e.g., fingers) of the EHR user 104 is detected, while still allowing the health information pane 204 to be visible. In the embodiment, the assistant overlay pane 502 can display a coordinate grid, wherein the coordinate grid is indicative of value ranges for the multidimensional value. In an example (as will be described in greater detail herein below), where the EHR user 104 is updating or entering a multidimensional value indicative of color, the assistant overlay pane 502 can include a graphic that is representative of a two-dimensional space of two dimensions of color (e.g., hue and lightness). As the EHR user 104 moves his or her fingers along the graphic, the assistant overlay pane 502 can further display a color result, where the color result is based upon changes of the input of the EHR user 104.

Further, in another embodiment, the assistant overlay pane 502 can include information indicative of decision support for the EHR user 104, wherein the information includes normal and abnormal values (for the multidimensional value). For the "BLOOD PRESSURE" field 216, for example, the assistant overlay pane 502 can include a coordinate grid overlay with areas shaded yellow or red to indicate, respectively, abnormal and severe blood pressure.

Figure 6:
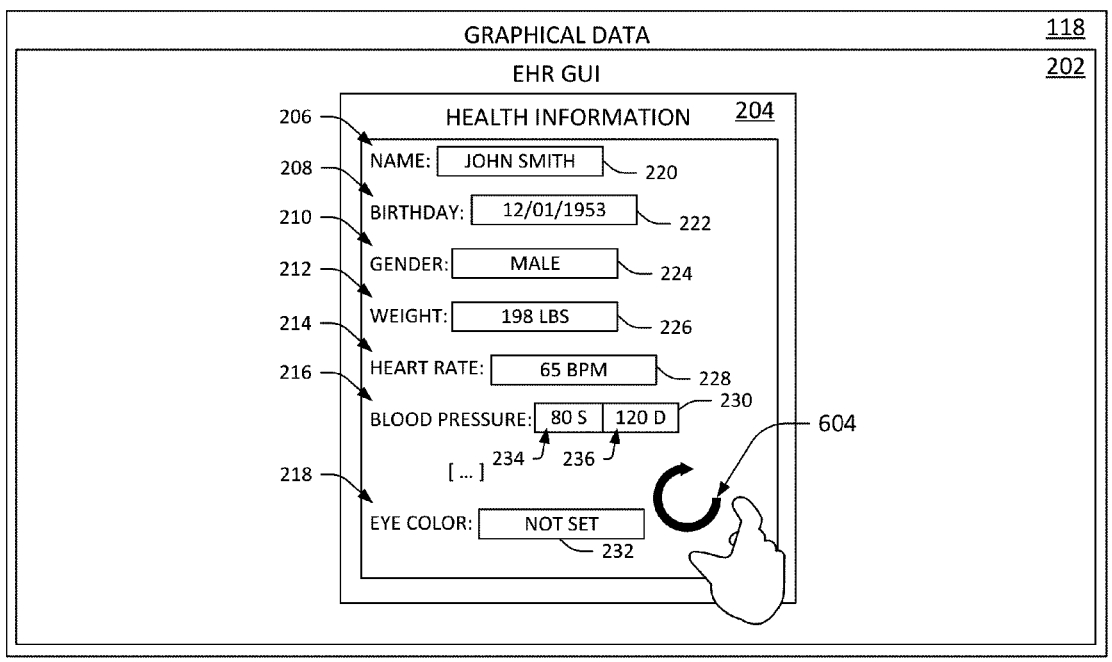
FIG. 6 depicts yet another exemplary graphical user interface of an EHR.

Additional details pertaining to the EHR user 104 updating or entering three or more dimensions of a multidimensional value that includes three or more dimensions is now set forth. As described previously, the dimensional input detection component 130 can be configured to detect that the EHR user 104 is updating or entering three or more dimensions of a multidimensional value that includes three or more dimensions. In an example shown in FIG. 6, the dimensional input detection component 130 has detected that the EHR user 104 is updating or entering three dimensions when the EHR user 104 taps and holds on a third value indicator 232 associated with the "EYE COLOR" field 218 with three fingers (e.g., an index finger, a middle finger, and a ring finger) of a hand of the EHR user 104. In the example, the third value indicator 232 includes a multidimensional value that includes three dimensions, 1) hue, 2) lightness, and 3) opacity. Similar to as described above, the dimensional input detection component 130 can be configured to assign a first finger (e.g., an index finger of the hand of the EHR user 104) to the hue and a second finger (e.g., a middle finger of the hand of the EHR user 104) to the lightness. Additionally, the dimensional input detection component 130 can be configured to assign a rotation measurement 604 to the opacity, where the rotation measurement 604 is based upon relative positions of the index finger and the middle finger of the hand of the EHR user 602.

The dimensional input detection component 130 is configured to monitor, as the EHR user 104 adjusts its gesture of the hand, changes in location of the fingers along the display, as well as rotation measurement. Based upon the changes, the dimensional input detection component 130 can update or enter a measurement for a respective dimension (e.g., hue, lightness, or opacity). Further, the dimensional input detection component 130 can cause the third value indicator 232 to display a color or text (that describes the color, e.g., "BROWN", "BLUE", etc.) that is correlative to the measurements calculated from the changes in location of the first finger, location of the second finger, and the rotation measurement.

It is contemplated that the dimensional input detection component 130 can be further configured to detect that the EHR user 104 is updating or entering two (out of the three) dimensions when the EHR user 104 taps and holds certain dimensional indicators of the third value indicator 232 associated with the "EYE COLOR" field 218 with two fingers (e.g., an index finger and a middle finger). In an example, the dimensional input detection component 130 can be configured to assign a first finger (e.g., the index finger of the hand of the EHR user 104) to the hue and a second finger (e.g., the middle finger of the hand of the EHR user 104) to the lightness. The dimensional input detection component 130 is further configured to monitor, as the EHR user 104 adjusts its gesture of the first finger and the second finger, changes in location of the fingers along the display. Based upon the changes, the dimensional input detection component 130 can update or enter a measurement for a respective dimension (e.g., hue and lightness). It can be ascertained that the dimensional input detection component 130 con be further configured to, when the EHR user 104 indicates that it is editing a multidimensional value that includes more than two dimensions, determine a number of dimensions to update or enter based on how many fingers the EHR user 104 places on the multidimensional value.

Figure 7:
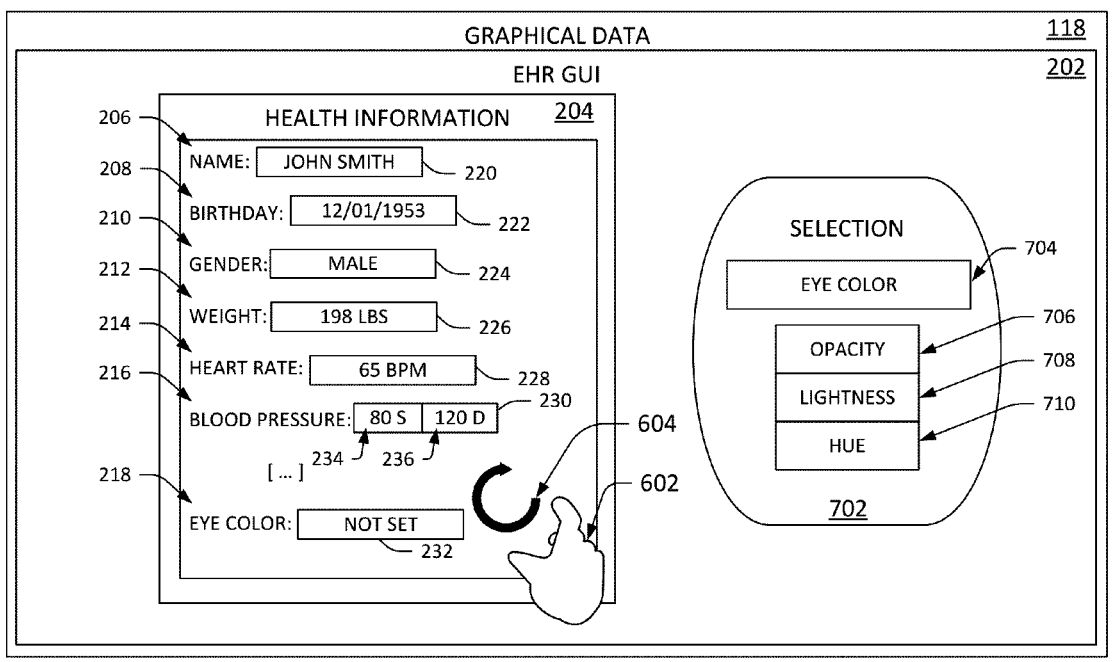
FIG. 7 depicts an exemplary selection pane.

Additional detail pertaining to a selection pane is now set forth. With reference to FIG. 7, the client EHR 116 can be configured to cause a selection pane 702 to be displayed while the dimensional input detection component 130 is being executed by the processor 110. More particularly, the selection pane 702 can be displayed when the dimensional input detection component 130 detects that the EHR user 104 has indicated that he or she is updating or entering a number of dimensions of a multidimensional value that is less than a number of total dimensions that the multidimensional value includes.

For example, the selection pane 702 can be displayed when the dimensional input detection component 130 detects that the second value indicator 230 includes a multidimensional value that includes more than two dimensional indicators (when the EHR user 104 has indicated that it is updating or entering two dimensions). In another example, the selection pane 702 can be displayed when the dimensional input detection component 130 detects that the EHR user 104 updating or entering one (or two) dimensions of multidimensional value that includes three or more dimensions. In an example shown in FIG. 7, the dimensional input detection component 130 has detected that the EHR user 104 is updating or entering two of three dimensions of the third value indicator (that contains the multidimensional value that includes three dimensions, 1) hue, 2) lightness, and 3) opacity) indicative of the "EYE COLOR" field 218 of a patient. Responsive to detecting that the EHR user 104 is updating or entering at least one of the three dimensions of the third value indicator, the client EHR 116 can cause the selection pane 702 to be displayed. The selection pane 702 includes a first indicator 704 that indicates that the EHR user 104 is updating or entering a value for the "EYE COLOR" 218. Additionally, the selection pane 702 includes a second indicator 706 (that indicates the opacity dimension); a third indicator 708 (that indicates the lightness dimension); and a fourth indicator 710 (that indicates the hue dimension). The selection pane 702 is configured to allow the EHR user 104 to select which dimensions (indicated by the second indicator 706, the third indicator 708, and the fourth indicator 710) to update or enter (based upon the, e.g., touch input of the EHR user 104). For example, responsive to the EHR user 104 selecting the second indicator 706 (with, e.g., an index finger) and the third indicator 708 (with, e.g., a middle finger), the multidimensional input detection component 130 is configured to facilitate an updating or entering of data for the opacity and lightness dimensions similar to as described above. More particularly, the dimensional input detection component 130 is further configured to monitor, as the EHR user 104 adjusts its gesture of the index finger and the middle finger, changes in location of the fingers along the display. Based upon the changes, the dimensional input detection component 130 can update or enter a measurement for a respective dimension (e.g., opacity and lightness).

It is to be understood that in another embodiment, in lieu of the client EHR 116 causing a selection pane 702 to be displayed, the second indicator 706, the third indicator 708, and the fourth indicator 710 can be displayed alongside the third value indicator 232. In the embodiment, changes to dimensions (indicated by the indicators 706-710) can be facilitated as described previously.

Figure 8:
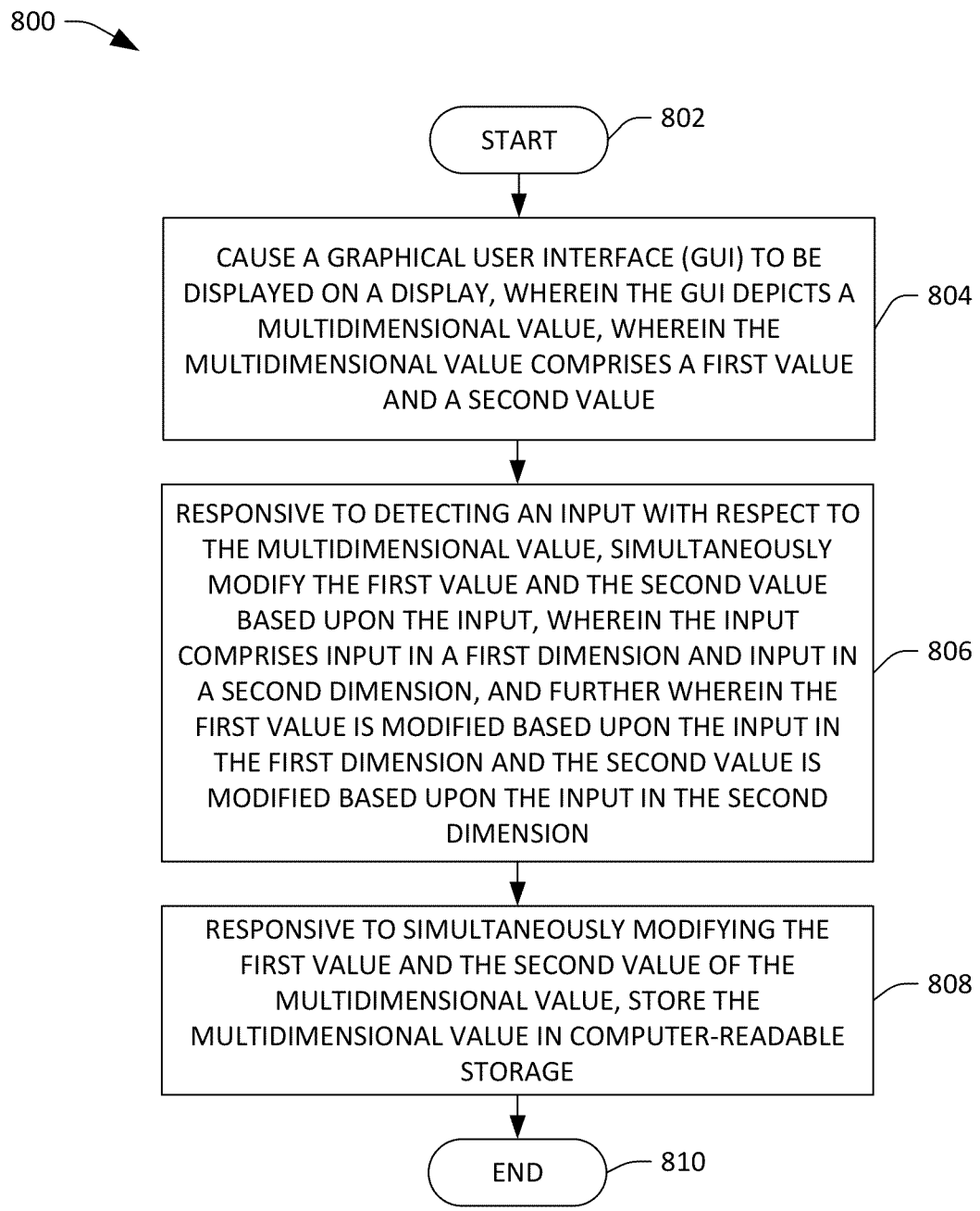
FIG. 8 is a flow diagram illustrating an exemplary methodology for updating patient data based upon input of an EHR user by way of a graphical user interface.

FIG. 8 depicts an exemplary methodology pertaining to updating patient data based upon input of an EHR user by way of a graphical user interface. While the methodology is shown and described as being a series of acts that are performed in a sequence, it is to be understood and appreciated that the methodology is not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

The methodology 800 is performed at a client computing device that executes a client EHR. The methodology 800 starts at 802, and at 804, the client EHR causes a graphical user interface (GUI) to be displayed on a display, wherein the GUI depicts a multidimensional value, wherein the multidimensional value comprises a first value and a second value. In an example, the multidimensional value is a blood pressure measurement of a patient. Further, the first value can be a systolic blood pressure measurement of the patient, and the second value can be a diastolic blood pressure measurement of the patient.

At 806, responsive to detecting an input with respect to the multidimensional value, the client EHR is configured to simultaneously modify the first value and the second value based upon the input, wherein the input comprises input in a first dimension and input in a second dimension, and further wherein the first value is modified based upon the input in the first dimension and the second value is modified based upon the input in the second dimension In the example, the input can comprise a touch and drag (by way of a touch input) of a EHR user. More particularly, the touch and drag can begin at the multidimensional value (as depicted on the GUI) and end at a region down and to the right of the multidimensional value. Responsive to detecting the touch and the drag, the client EHR can simultaneously, for example, increase the first value (the systolic blood pressure measurement of the patient) and decrease the second value (the diastolic blood pressure measurement of the patient).

At 808, responsive to simultaneously modifying the first value and the second value of the multidimensional value, the client EHR is configured to store the multidimensional value in computer-readable storage. In the example, the multidimensional value (the blood pressure) can be stored in a server computing device. The methodology 800 completes at 808.

Figure 9:
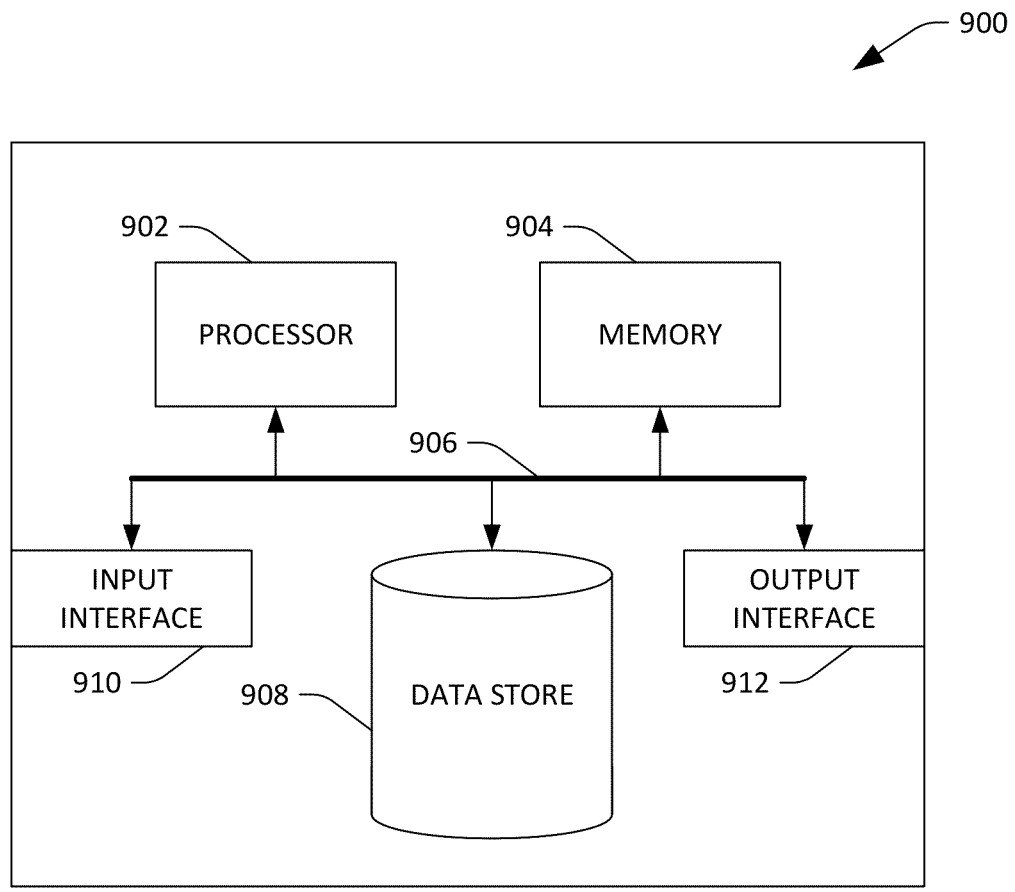
FIG. 9 is an exemplary computing device.

Referring now to FIG. 9, a high-level illustration of an exemplary computing device 900 that can be used in accordance with the systems and methodologies disclosed herein is illustrated. For instance, the computing device 900 may be used in a system that facilitates updating patient data based upon input of an EHR user by way of a GUI is illustrated. The computing device 900 includes at least one processor 902 that executes instructions that are stored in a memory 904. The instructions may be, for instance, instructions for implementing functionality described as being carried out by one or more components discussed above or instructions for implementing one or more of the methods described above. The processor 902 may access the memory 904 by way of a system bus 906. In addition to storing executable instructions, the memory 904 may also store patient data, etc.

The computing device 900 additionally includes a data store 908 that is accessible by the processor 902 by way of the system bus 906. The data store 908 may include executable instructions, databases, etc. The computing device 900 also includes an input interface 910 that allows external devices to communicate with the computing device 900. For instance, the input interface 910 may be used to receive instructions from an external computer device, from a user, etc. The computing device 900 also includes an output interface 912 that interfaces the computing device 900 with one or more external devices. For example, the computing device 900 may display text, GUIs, etc. by way of the output interface 912.

It is contemplated that the external devices that communicate with the computing device 900 via the input interface 910 and the output interface 912 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 900 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 900 may be a distributed system. Thus, for instance, several devices may be in communication by way of a network connection and may collectively perform tasks described as being performed by the computing device 900.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

While the examples provided herein have pertained to an EHR, it is to be understood that the techniques for simultaneously altering multiple dimensions of a multi-dimensional value are applicable in other scenarios and applications. For instance, the techniques described herein can be well-suited for simultaneously altering or entering two or more entries in a table by way of a spreadsheet application. In another example, integers and decimals of a number can be simultaneously modified in a mathematics application. Other examples will be readily contemplated.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A computing device comprising:
   a touch-sensitive display;
   at least one processor that is operably coupled to the touch-sensitive display; and
   memory that stores a client electronic health records (EHR) application that, when executed by the at least one processor, causes the at least one processor to perform acts comprising:
   causing a graphical user interface (GUI) for the client EHR application to be displayed on the touch-sensitive display, wherein the GUI depicts a multidimensional value pertaining to a patient, wherein the multidimensional value comprises a first value and a second value;
   responsive to detecting a drag of a finger across a surface of the touch-sensitive display, wherein the drag of the finger comprises a change in position of the finger along a first axis and a change in position of the finger along a second axis that is orthogonal to the first axis that are simultaneously received by the GUI, simultaneously modifying the first value and the second value as the finger is dragged across the surface of the touch-sensitive display, wherein the first value is modified based upon the change in position of the finger along the first axis as the finger is dragged across the surface of the touch-sensitive display and the second value is modified based upon the change in position of the finger along the second axis as the finger is dragged across the surface of the touch-sensitive display; and
   subsequent to simultaneously modifying the first value and the second value of the multidimensional value, causing the multidimensional value to be stored in computer-readable storage of a server EHR application.

2. The computing device of claim 1, the acts further comprising:
   responsive to detecting the drag of the finger across the surface of the touch-sensitive display, altering the GUI to visually depict the first value and the second value being simultaneously modified as the finger is dragged across the surface of the touch-sensitive display.

3. The computing device of claim 1, wherein the multidimensional value is indicative of a blood pressure measurement.

4. The computing device of claim 3, wherein the first value is indicative of a systolic blood pressure measurement.

5. The computing device of claim 4, wherein the second value is indicative of a diastolic blood pressure measurement.

6. The computing device of claim 1, the acts further comprising:
   responsive to detecting the drag of the finger across the surface of the touch-sensitive display, causing the GUI to depict an assistant overlay pane, wherein the assistant overlay pane depicts assignment information.

7. A method performed by a client computing device that executes a client electronic health record application (EHR), the method comprising:
   causing a graphical user interface (GUI) for the client EHR application to be displayed on a touch-sensitive display, wherein the GUI depicts a multidimensional value pertaining to a patient, wherein the multidimensional value comprises a first value and a second value;
   responsive to detecting with a drag of a finger across a surface of the touch-sensitive display, wherein the drag of the finger comprises a change in position of the finger along a first axis and a change in position of the finger along a second axis that is orthogonal to the first axis that are simultaneously received by the GUI, simultaneously modifying the first value and the second value as the finger is dragged across the surface of the touch-sensitive display, wherein the first value is modified based upon the change in position of the finger along the first axis as the finger is dragged across the surface of the touch-sensitive display and the second value is modified based upon the change in position of the finger along the second axis as the finger is dragged across the surface of the touch-sensitive display; and subsequent to simultaneously modifying the first value and the second value of the multidimensional value, causing the multidimensional value to be stored in computer-readable storage of a server EHR application.

8. The method of claim 7, further comprising:

responsive to detecting the drag of the finger across the surface of the touch-sensitive display, altering the GUI to visually depict the first value and the second value being simultaneously modified as the finger is dragged across the surface of the touch-sensitive display.

9. The method of claim 7, wherein the multidimensional value is indicative of a blood pressure measurement.

10. The method of claim 9, wherein the first value is indicative of a systolic blood pressure measurement.

11. The method of claim 10, wherein the second value is indicative of a diastolic blood pressure measurement.

12. The method of claim 7, further comprising:

responsive to detecting the drag of the finger across the surface of the touch-sensitive display, causing the GUI to depict an assistant overlay pane, wherein the assistant overlay pane depicts assignment information.

13. A computing device comprising:

a touch-sensitive display;

at least one processor that is operably coupled to the touch-sensitive display; and memory that stores a client electronic health records (EHR) application that, when executed by the at least one processor, causes the at least one processor to perform acts comprising:

causing a graphical user interface (GUI) for the client EHR application to be displayed on the touch-sensitive display, wherein the GUI depicts a multidimensional value pertaining to a patient, wherein the multidimensional value comprises a first value, a second value, and a third value;

responsive to detecting a drag of a finger across a surface of the touch-sensitive display, wherein the drag of the finger comprises a change in position of the finger along a first axis, a change in position of the finger along a second axis that is orthogonal to the first axis, and a change in position of the finger along a third axis that is orthogonal to both the first axis and the second axis that are simultaneously received by the GUI, simultaneously modifying the first value, the second value, and the third value as the finger is dragged across the surface of the touch-sensitive display, wherein the first value is modified based upon the change in position of the finger along the first axis as the finger is dragged across the surface of the touch-sensitive display, the second value is modified based upon the change in position of the finger along the second axis as the finger is dragged across the surface of the touch-sensitive display, and the third value is modified based upon the change in position of the finger along the third axis as the finger is dragged across the surface of the touch-sensitive display; and subsequent to simultaneously modifying the first value, the second value, and the third value of the multidimensional value, causing the multidimensional value to be stored in computer-readable storage of a server EHR application.

14. The computing device of claim 13, the acts further comprising:

responsive to detecting the drag of the finger across the surface of the touch-sensitive display, causing the GUI to depict a selection pane, and further wherein, responsive to receiving an additional input with respect to the selection pane, assigning the first value to the change in position of the finger along the first axis, wherein the assignment causes the first value to be modified based upon the change in position of the finger along the first axis.

15. The computing device of claim 13, the acts further comprising:

responsive to detecting the drag of the finger across the surface of the touch-sensitive display, altering the GUI to visually depict the first value, the second value, and the third value being simultaneously modified as the finger is dragged across the surface of the touch-sensitive display.

16. The computing device of claim 13, wherein the computing device is a tablet computing device.

17. The computing device of claim 1, wherein the server EHR application executes on a cloud-based computing device.

18. The computing device of claim 1, wherein the computing device is a tablet computing device.

19. The method of claim 7, wherein the computing device is a tablet computing device.

20. The method of claim 7, wherein the server EHR application executes on a cloud-based computing device.

* * * * *